United States Patent
Ilenda et al.

(10) Patent No.: US 7,244,775 B2
(45) Date of Patent: Jul. 17, 2007

(54) DAMAGE RESISTANT COATINGS, FILMS AND ARTICLES OF MANUFACTURE CONTAINING CROSSLINKED NANOPARTICLES

(75) Inventors: Casmir S. Ilenda, Holland, PA (US); Michael Louis Spera, Mohnton, PA (US); Andrew T. Daly, Sinking Spring, PA (US); Robert H. Gore, Southampton, PA (US); Wayne Devonport, Doylestown, PA (US); Eric G. Lundquist, North Wales, PA (US); Paul Francis Reeve, Valbonne (FR); James R. Lesniak, Merrillville, IN (US); Ethan S. Simon, Abington, PA (US); Warren H. Machleder, deceased, late of Blue Bell, PA (US); by Jenifer Lyn Machleder, legal representative, Fremont, CA (US); by Eric Michael Machleder, legal representative, San Francisco, CA (US)

(73) Assignee: Rohm and Haas Company, Philadelphia, PA (US)

( * ) Notice: Subject to any disclaimer, the term of this patent is extended or adjusted under 35 U.S.C. 154(b) by 502 days.

(21) Appl. No.: 10/461,971

(22) Filed: Jun. 13, 2003

(65) Prior Publication Data

US 2004/0063817 A1    Apr. 1, 2004

Related U.S. Application Data

(60) Provisional application No. 60/414,597, filed on Sep. 30, 2002.

(51) Int. Cl.
*C08K 9/00* (2006.01)
(52) U.S. Cl. ............... 523/202; 523/201; 523/205; 523/220; 524/539
(58) Field of Classification Search ............ 523/220, 523/201–202, 205; 524/539
See application file for complete search history.

(56) References Cited

U.S. PATENT DOCUMENTS 4,450,255 A * 5/1984 Baney .................. 524/430
4,487,855 A   12/1984 Shih et al.
4,514,552 A    4/1985 Shay et al.
4,560,714 A   12/1985 Gajria et al.
4,746,455 A    5/1988 Matsuda et al.
5,064,923 A   11/1991 Kashihara et al.
5,290,654 A    3/1994 Sacripante et al.
5,538,717 A    7/1996 La Poterie
5,863,996 A    1/1999 Graham
5,874,111 A    2/1999 Maitra et al.
6,020,419 A    2/2000 Bock et al.
6,194,530 B1   2/2001 Klesse et al.
6,268,222 B1   7/2001 Chandler et al.
6,329,060 B1 * 12/2001 Barkac et al. ........... 428/423.1
6,329,446 B1  12/2001 Sacripante et al.
6,387,519 B1   5/2002 Anderson et al.
6,878,776 B1 *  4/2005 Pascault et al. ............ 525/113
6,939,922 B2 *  9/2005 Beckley et al. .......... 525/329.7
2002/0065208 A1  5/2002 Aubay et al.
2002/0164297 A1 11/2002 Ferrari et al.
2002/0177522 A1 11/2002 Alexander, IV et al.
2002/0193521 A1 12/2002 Cruz et al.
2003/0055178 A1  3/2003 Gore et al.
2003/0059599 A1  3/2003 Beckley et al.
2003/0162890 A1  8/2003 Kalantar et al.

FOREIGN PATENT DOCUMENTS

| EP | 0 250 183 | 12/1987 |
|---|---|---|
| EP | 0 250 887 | 1/1988 |
| EP | 1 245 587 | 10/2002 |
| EP | 1 245 643 | 10/2002 |
| WO | WO 93/00376 | 1/1993 |
| WO | WO 99/01522 | 1/1999 |
| WO | WO 0059953 | 10/2000 |
| WO | WO 01/90226 | 11/2001 |

* cited by examiner

*Primary Examiner*—Peter Szekely
(74) *Attorney, Agent, or Firm*—Ron Bakule; Kim Jessum

(57) ABSTRACT

A method for imparting damage resistance to a coating, film or article of manufacture comprising adding crosslinked polymeric nanoparticles having a size range of 1-100 nm in diameter to said coating, film or article of manufacture.

18 Claims, No Drawings

DAMAGE RESISTANT COATINGS, FILMS AND ARTICLES OF MANUFACTURE CONTAINING CROSSLINKED NANOPARTICLES

CROSS REFERENCE TO RELATED PATENT APPLICATIONS

This is a non-provisional application of prior pending U.S. provisional application Ser. No. 60/414.597 filed Sep. 30, 2002.

BACKGROUND OF THE INVENTION

Damage resistance is a desired property in most coatings, films or articles of manufacture. Coatings, films, and articles of manufacture are subject to stresses caused by environmental agents such as sunlight and adverse weather conditions and physical agents and chemical agents as a result of spills. These stresses create considerable wear and tear and may lead to chipping, marring, crocking, scratching, etching or staining of the surface of the coating, film or article of manufacture. Inorganic and Polymeric Particles have been used to create coatings, films and articles of manufacture having resistance to these environmental, physical and chemical stresses. Typically, said particles are in the size range of 100-1000 nm. The benefits of inorganic and polymeric particles include at least one of the following improved surface properties: wetting and sheeting, quick drying, uniform drying, soil removal, self-cleaning, anti-spotting, anti-soil deposition, cleaner appearance, enhanced gloss, enhanced color, minor surface defect repair, smoothness, anti-hazing, modification of surface friction, release of actives, transparency (e.g., in the case of glass and the like) and damage resistance.

However, there have been many problems associated with developing coatings, films or articles of manufacture with the aforementioned properties. These problems include limit to single use protection, insufficient coverage, surface roughness and/or flaking of coating during use, a limit on surfaces that can be modified, and lack of durability or damage resistance.

The art has attempted to solve these problems. U.S. Pat. No. 5,034,432, to Ueno et al., discloses powder coatings including resin microparticles having a 0.001 micron to 10 micron average diameter to improve stain resistance and weather resistance. However, Ueno et al, does not disclose any example of a microparticle smaller than 0.16 microns (160 nanometers) in diameter. Further, Ueno discloses that it is difficult to make particles approaching a 0.001 micron average particle diameter. Further, the effective concentration of microparticles for stain resistant and weather resistant coating powders is inversely proportional to the microparticle average particle diameter. Finally, Ueno et al. does not disclose compositions comprising microparticles which exhibit surface migration.

In EP 0832947A2, Oermann discloses the use of 1 to 1000 nm inorganic particles in a coating composition for the production of scratch resistant clearcoat automotive coatings.

U.S. Pat. No. 6,387,519 (U.S.'519)to Anderson discloses cured coatings comprising particles having an average particle size of 1 to less than 1000 nm prior to incorporation into the coating composition. Further, said particles are located in a greater concentration in the surface region of the cured composition. Said particles can be formed from a wide variety of materials, such as ceramic materials, metallic materials, silica, alumina, zirconia, siloxanes, metal oxides, and organic polymers such as polyethylene, polycarbonates, acrylic polymers, styrene, and polyamides. See Col 9, lines 63-67; Col 10, lines 1-10; Col 10, lines 39-46; Col 12, lines 59-67; Col 13, lines 1-23. Said organic polymers are not crosslinked, but can become part of the cured crosslinked coating.

Specifically, U.S.'519 discloses inorganic particles and modified inorganic particles, particularly silica and siloxanes, for use in automotive clearcoat compositions.

U.S. Pat. No. 5,538,717 to LaPoterie discloses aqueous based nail polish formulations that are damage resistant. La Poterie discloses the use of aqueous anionic dispersions that are composed of 2 to 40 nm anionic polyester-polyurethane and polyether-polyurethane particles. The particles described by La Poterie are not crosslinked and do not include acrylic and styrenic compositions. Further, La Porterie did not disclose the use of combinations of inorganic nanoparticles and polymer nanoparticles in aqueous nail polish formulations.

Applicants have now discovered that damage resistant coatings, films or articles of manufacture can be prepared using crosslinked organic polymeric nanoparticles having a diameter of 1-100 nm alone or in combination with inorganic nanoparticles. Further, applicant's crosslinked polymeric nanoparticles are useful in a wide variety of applications such as industrial coatings, floor polishes, automotive coatings and personal care applications such as nail polish.

SUMMARY OF THE INVENTION

The present invention relates to a method for imparting damage resistance to a coating, film or article of manufacture comprising adding crosslinked polymeric nanoparticles (PNPs) alone or in combination with inorganic nanoparticles, said nanoparticles having a size range of 1-100 nm in diameter, to said coating, film or article of manufacture.

The present invention further relates to a damage resistant coating, film, or article of manufacture comprising crosslinked polymeric nanoparticles (PNPs) alone or in combination with inorganic nanoparticles, said nanoparticles having a size range of 1-100 nm in diameter.

The following terms have the following meanings herein:

As used herein, the term "article" or "article of manufacture" refers to any molded, extruded or shaped articles, such as polyolefin pipes, sheets, films, luggage, interior and exterior automotive parts, foamed articles for insulation and deck furniture, molded composites, cast articles, such as films, multi-layer films, and prepregs, such as those used for making printed circuit boards (PCB's) or printed wiring boards (PWBs).

As used herein, the term "average particle diameter", when referring to PNPs means that average diameter as determined by gel permeation chromatography (GPC) or using standard dynamic light scattering techniques.

As used herein the term "polymeric nanoparticle" (PNP) means macromolecules that contain crosslinking having a particle size of 1-100 nm. Said crosslinking is at a level of 1-100%.

As used herein, the term "curable component or polymer" refers to any solid or liquid organic binder or resin material that can be used to make a shaped article, including both thermosetting and thermoplastic polymers or resins and natural and synthetic polymers or resins.

As used herein, the term "cured surfaces" refers to the surfaces of cured coatings, cured floor care compositions, cured films and cured articles.

As used herein, the term "damage" includes abrasion, crocking, marring, gouging, scratching and defacement, such as metal staining, of a coating, film or article.

As used herein, the term "non-film forming" means a substance which does not flow on a hot plate at 350 degrees F.

As used herein, the term "PNP particle dispersion" means a physical state of matter that includes at least two phases wherein a first phase is distributed in a second phase, the second phase being a continuous medium.

As used herein, the terms "solvent" and "polymerization medium" can be used interchangeably.

As used herein, the term "PNP concentrate" means a solid or liquid dispersion of PNPs in a polymer, curable component or resin according to the present invention.

As used herein, the term "Tg" refers to the glass transition temperature as determined using known differential scanning calorimetry (DSC) methods.

As used herein, the following abbreviations shall have the following meanings, unless the context clearly indicates otherwise: C=centigrade; μm=micron; UV=ultraviolet; rpm=revolutions per minute; nm=nanometer; J=joules; cc=cubic centimeter; g=gram; wt %=weight percent; L=liter; mL=milliliter; MIAK=methyl iso-amyl ketone; MIBK=methyl iso-butyl ketone; BA=butyl acrylate; AA=acrylic acid; IA=itaconic acid, MAA=methacrylic acid; DMA=dimethacrylate; PMA=poly(methyl acrylate); EG=ethylene glycol; DPG=dipropylene glycol; DEGDMA=diethylene glycol dimethacrylate; EGDMA=ethylene glycol dimethacrylate, DPEPA=dipentaerythritol pentaacrylate; HEMA=hydroxyethyl methacrylate; IBMA=isobutyl methacrylate; MAPS=MATS or MAPS=(trimethoxysilyl)propyl methacrylate; MMA=methyl methacrylate; PPG=polypropyleneglycol; PGDMA=propyleneglycol dimethacrylate; DVB=divinyl benzene; TMPTMA=trimethylolpropane trimethacrylate, TMPTA=trimethylolpropane triacrylate, SMA=stearyl methacrylate, LMA=lauryl methacrylate, GMA=glycidyl methacrylate.

As used herein, the term "(meth)acrylic" includes both acrylic and methacrylic and the term "(meth)acrylate" includes both acrylate and methacrylate. Likewise, the term "(meth)acrylamide" refers to both acrylamide and methacrylamide. "Alkyl" includes straight chain, branched and cyclic alkyl groups.

DETAILED DESCRIPTION OF THE INVENTION

The present invention relates to a method for imparting damage resistance to a coating, film or article of manufacture comprising adding crosslinked polymeric nanoparticles (PNPs) alone or in combination with inorganic nanoparticles, said nanoparticles having a size range of 1-100 nm in diameter, to said coating, film or article of manufacture.

The present invention relates to a damage resistant coating, film, or article of manufacture comprising crosslinked polymeric nanoparticles (PNPs) alone or in combination with inorganic nanoparticles, said nanoparticles having a size range of 1-100 nm in diameter. Further, the present invention provides compositions comprising crosslinked polymeric nanoparticles (PNPs) alone or in combination with inorganic nanoparticles, said nanoparticles having a size range of 1-100 nm in diameter used to make damage resistant coatings, films, or articles of manufacture.

Preferably, the crosslinked PNPs of the present invention have an average particle diameter of 1 to 100 nm, more preferably from 1 to 50 nm, most preferably from 1 to 30 nm.

The crosslinked PNPs of the present invention may be formed by polymerization techniques known to those skilled in the art. These techniques include, but are not limited to, condensation polymerization, cationic polymerization, ring opening metathesis polymerization, anionic polymerization and free radical polymerization. The most preferred technique is the free radical addition polymerization of a radical polymerizable monomer and at least one crosslinking monomer.

The crosslinked PNPs of the present invention preferably contain from 1-100% crosslinker by weight, more preferably 2-85% crosslinker, and most preferably 5-50% crosslinker.

Suitable multi-ethylenically-unsaturated crosslinking monomers useful in the present invention include, but are not limited to, di-, tri-, tetra-, or higher multi-functional ethylenically unsaturated monomers such as ethyleneglycol diacrylate, trimethylolpropane triacrylate (TMPTA), allyl methacrylate (ALMA), ethyleneglycol dimethacrylate (EGDMA), DEGDMA, propyleneglycol dimethacrylate, propyleneglycol diacrylate, TMPTMA, 2,2-dimethylpropane-1,3-diacrylate, 1,3-butylene glycol diacrylate, 1,3-butylene glycol dimethacrylate, 1,4-butanediol diacrylate, diethylene glycol diacrylate, diethylene glycol dimethacrylate, 1,6-hexanediol diacrylate, 1,6-hexanediol dimethacrylate, tripropylene glycol diacrylate, triethylene glycol dimethacrylate, tetraethylene glycol diacrylate, polyethylene glycol 200 diacrylate, tetraethylene glycol dimethacrylate, polyethylene glycol dimethacrylate, ethoxylated bisphenol A diacrylate, ethoxylated bisphenol A dimethacrylate, polyethylene glycol 600 dimethacrylate, poly(butanediol) diacrylate, pentaerythritol triacrylate, trimethylolpropane triethoxy triacrylate, glyceryl propoxy triacrylate, pentaerythritol tetraacrylate (PETTA), pentaerythritol tetramethacrylate (PETMA), and mixtures thereof. Other crosslinkers useful in the present invention may include DVB, vinyl urethanes, diallyl ethers, diallyl esters, vinyl polyesters, trivinylbenzene, divinyltoluene, divinylpyridine, divinylnaphthalene and divinylxylene, diethyleneglycol divinyl ether, bisacrylamide, triallyl cyanurate and trivinylcyclohexane.

For use in high-temperature resistant applications with silicon-containing resins, crosslinkers include, but are not limited to, silyl group-containing monomers such as divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, siloxane-containing monomers such as dimethyl vinyl disiloxane, poly(methyl vinyl siloxane), poly(vinyl hydro siloxane), poly (phenyl vinyl siloxane) and mixtures thereof.

Preferred Crosslinkers include, but are not limited to, DVB, TMPTA, TMPTMA, EGDMA, ALMA, bisacrylamide, and DEGDMA.

Polymerizable monomers useful in the practice of the present invention include, but are not limited to, alkyl (meth)acrylates, alicyclic (meth)acrylates, (meth)acrylamides, vinyl acetates, alkenyl (meth)acrylates, aryl (meth)acrylates, alkylaryl (meth)acrylates, fluro alkyl (meth)acrylates, -vinyl aromatic monomers, vinyl acetate, (meth) acrylic acid, and substituted ethylene monomers.

Preferred alkyl (meth)acrylates useful in making the PNPs of the present invention include, for example, substituted and unsubstituted methyl methacrylate ("MMA"), methyl acrylate, ethyl acrylate, propyl methacrylate, butyl methacrylate ("BMA"), butyl acrylate ("BA"), IBMA, IBOMA, IA, GMA, SMA, hexyl methacrylate, cyclohexyl methacrylate, cyclohexyl acrylate, 2-ethylhexyl acrylate ("EHA"), 2-ethylhexyl methacrylate, octyl methacrylate, decyl methacrylate, isodecyl methacrylate, undecyl methacrylate, dodecyl methacrylate, tridecyl methacrylate, tetradecyl methacrylate, pentadecyl methacrylate, hexadecyl methacrylate, heptadecyl methacrylate, octadecyl methacrylate, nonadecyl methacrylate, cosyl methacrylate, eicosyl methacrylate and mixtures thereof.

Useful substituted alkyl (meth)acrylate monomers for making PNPs containing acid functional monomers may include those with one or more hydroxyl groups in the alkyl radical, such as hydroxyalkyl (meth)acrylate monomers having a substituted alkyl group selected from the group consisting of $(C_2-C_6)$alkyl, branched and unbranched alkyl groups. Likewise, where hydroxyl group containing monomers or monomers containing acetoacetoxy groups are used to make PNPs, acid functional monomers can be added to react with those groups. Examples of these monomers are hydroxyalkyl (meth)acrylate 2-hydroxyethyl methacrylate ("HEMA"), 2-hydroxyethyl acrylate ("HEA"), 2-hydroxypropyl methacrylate and acetoacetoxy methacrylate.

Other substituted (meth)acrylate monomers useful in the present invention may include silicon-containing monomers such as γ-propyl tri$(C_1-C_6)$ alkoxysilyl (meth)acrylate, γ-propyl tri$(C_1-C_6)$ alkylsilyl (meth)acrylate, γ-propyl di$(C_1-C_6)$ alkoxy $(C_1-C_6)$alkylsilyl (meth)acrylate, γ-propyl di$(C_1-C_6)$alkyl$(C_1-C_6)$alkoxysilyl (meth)acrylate, vinyl tri $(C_1-C_6)$alkoxysilyl (meth)acrylate, vinyl di$(C_1-C_6)$alkoxy $(C_1-C_6)$alkylsilyl (meth)acrylate, vinyl $(C_1-C_6)$ alkoxydi $(C_1-C_6)$alkylsilyl (meth)acrylate, vinyl tri$(C_1-C_6)$alkylsilyl (meth)acrylate, and mixtures thereof.

Vinylaromatic monomers useful as polymerizable monomers in the practice of the present invention include styrene ("STY"), α-methylstyrene, vinyltoluene, p-methylstyrene, ethylvinylbenzene, vinylnaphthalene, vinylxylenes, chlorostyrene, bromostyrene, fluorostyrene, and mixtures thereof.

Other polymerizable monomers useful in the practice of the present invention include cyclopent(adi)ene, allylic monomers, vinyl acetate, vinyl formamide, vinyl chloride, vinyl fluoride, vinyl bromide, vinylidene chloride, vinylidene fluoride and vinylidene bromide. However, it is preferable to use those monomers which can be polymerized using initiators commonly used to polymerize (meth)acrylate monomers, e.g. dibenzoyl peroxide.

Preferred Polymerizable Monomers include, but are not limited to, BA, BMA, IBOMA, MMA, MA, MAA, AA, IA, Styrene, SMA, LMA, GMA, and HEMA.

Initiators useful in the free radical polymerization of the present invention include, for example, one or more of: peroxyesters, dialkylperoxides, alkylhydroperoxides, persulfates, azoinitiators, redox initiators and the like. Useful free radical initiators include, but are not limited to: benzoyl peroxide, t-butyl peroctoate, t-amyl peroxypivalate, cumene hydroperoxide, and azo compounds such as azoisobutyronitrile and 2,2'-azobis (2-methylbutanenitrile). Preferably, the free radical initiator is t-amyl Peroxypivalate. The amount of the free radical initiator used is typically from 0.05 to 10% by weight, based on the weight of total monomer.

Control of particle size and distribution can be augmented by such methods as choice of solvent, choice of initiator, total solids level, initiator level, type and amount of multifunctional monomer, type and amount of chain transfer agent, and reaction conditions. Chain transfer reagents can optionally be used to prepare the polymers useful in the present invention. Suitable chain transfer agents include, for example: mercaptopropionic acid, alkyl mercaptans such as dodecyl mercaptan, and aromatic hydrocarbons with activated hydrogens such as toluene.

Solvents or polymerization medium useful in the practice of the present invention include, but are not limited to, hydrocarbons, such as alkanes, fluorinated hydrocarbons, aromatic hydrocarbons, ethers, ketones, esters, alcohols, water and mixtures thereof. Particularly suitable solvents include mesitylene, xylenes, diphenyl ether, gamma butyrolactone, ethyl acetate, ethyl lactate, propyleneglycol, monomethylether acetate, caprolactone, 2-heptanone, methylisobutylketone, diisobutylketone, methylethylketone, isobutyl acetate, propyleneglycol monomethylether, and alkyl alcohols such as hexanol, t-butanol, and isopropanol.

Inorganic nanoparticles useful in the practice of the present invention include, but are not limited to, clays, silica (colloidal, fumed, amorphous,), silica sols, titanium dioxide, metals (alumina and zirconia), metal oxides (eg cesium oxide, alumina oxide, yttrium oxide, antimony oxide), metal nitrides, metal carbides, metal sulfides, metal silicates, metal borides, metal carbonates, zeolites and carbon nanotubes. The particle size of the inorganic particles is preferably between 1 and 1000 nm, more preferably between 1 and 100 and most preferably between 2 and 50 nm.

The following non limiting examples illustrate how to prepare the crosslinked PNPs of the present invention.

EXAMPLE 1

Preparation of Crosslinked Polymeric Nanoparticle

A 500 mL reactor was fitted with a thermocouple, a temperature controller, a purge gas inlet, a water-cooled reflux condenser with purge gas outlet, a stirrer, and an addition funnel. To the addition funnel was charged 201.60 g of a monomer mixture consisting of 18.00 g methyl methacrylate (100% purity), 2.00 g diethyleneglycol dimethacrylate (100% purity), 1.60 g of a 75% solution of t-amyl peroxypivalate in mineral spirits and 180.00 g diisobutyl ketone ("DIBK"). The reactor, containing 180.00 g DIBK was then flushed with nitrogen for 30 minutes before applying heat to bring the contents of the reactor to 75° C. When the contents of the reactor reached 75° C., the monomer mixture in the addition funnel was uniformly charged to the reactor over 90 minutes. Thirty minutes after the end of the monomer mixture addition, the first of two chaser aliquots, spaced thirty minutes apart and consisting of 0.06 g of a 75% solution of t-amyl peroxypivalate in mineral spirits and 2.00 g DIBK, was added. At the end of the second chaser aliquot, the contents of the reactor were held 2½ hours at 80° C. to complete the reaction. The resulting polymer was isolated by precipitation with heptane, collected by filtration and dried under vacuum to yield a white powder. This material was redissolved in propyleneglycol monomethylether acetate. The nanoparticles thus formed had a particle size distribution of from 0.8 to 5.0 nm with mean of 1.4 nm as determined by dynamic laser light scattering.

EXAMPLE 2

Preparation of Crosslinked Polymeric Nanoparticle

A 1000 mL reactor was fitted with a thermocouple, a temperature controller, a purge gas inlet, a water-cooled reflux condenser with purge gas outlet, a stirrer, and an addition tube. The reactor, containing 500 g of methyl ethyl ketone (MEK) solvent was flushed with nitrogen for 30 minutes before applying heat to bring the contents of the reactor to 80° C. When the contents of the reactor reached 80° C., a monomer mixture containing 90 g of methyl methacrylate (100% purity), 10 g of trimethylolpropane trimethacrylate, 5 g of a 75% solution of t-amyl peroxypivalate in mineral spirits, and 100 g MEK was uniformly charged to the reactor over 90 minutes. Sixty minutes after the end of the monomer mixture addition, the first of two chaser aliquots, spaced thirty minutes apart and consisting of 1 g of a 75% solution of t-amyl peroxypivalate in mineral spirits, was added. At the end of the second chaser aliquot, the contents of the reactor were held 6 hours at 80° C. to complete the reaction. The resulting polymer was isolated by removing the solvent under vacuum. The nanoparticles thus formed had a particle size distribution of from 2 to 20 nm.

EXAMPLE 3

Preparation of a Crosslinked Polymeric Nanoparticle

A monomer emulsion was made from a mixture of 100 g water, 1.60 g of 28% w/w solids ammonium lauryl sulfate (ALS), 68 g ethyl acrylate ("EA"), 17 g methyl methacrylate ("MMA"), 12.5 g divinyl benzene ("DVB"), and 5 g methacrylic acid ("MAA"). A reaction kettle containing 445 g water, 22.2 g of 28% w/w solids ALS and 0.37 g APS was heated to 85° C. under a nitrogen atmosphere. The monomer emulsion was fed to the kettle over 90 minutes. The reaction was held at 85° C. for 30 minutes after the end of the feed, and then cooled to 65° C. After cooling, 1.33 g of 10% iron sulfate ($FeSO_4$) was added. After 1 minute, 0.2 g of 70% t-BHP was added and after 2 minutes 0.10 g of 100% isoascorbic acid ("IAA") and the reaction held for 15 minutes. A second chaser system was added in the same sequence and over the same time period. The reaction was then cooled to ambient temperature and filtered through a 400 mesh sieve.

EXAMPLE 4

PNP Formulations

The PNPs of the present invention can be formulated as PNP particle dispersions or PNP concentrates in the form of liquids, in emulsion, dispersion or solution form. However, in article-forming or film-forming powders and powder coatings, PNPs, PNP particle dispersions in dispersion, emulsion or solution form, and PNP concentrates are dried for use. PNPs or PNP particle dispersions may be incorporated into a polymer component during a liquid dispersion or thermoplastic melt-blending process. Drying of PNPs or PNP particle dispersions can be accomplished in a known fashion by precipitating the PNPs followed by centrifugation, vacuum distillation or spray drying to form dried PNPs or their agglomerates. PNP particle dispersions can comprise liquid droplets, masses or powders. Liquid droplets may be formed by dispersing PNPs as solutions, dispersions, suspensions, emulsions or powders into an aqueous emulsion or an aqueous or solvent dispersion, solution or suspension of polymer or curable component. For forming powders and masses of PNP particle dispersions, the PNPs can be predispersed in the melt of polymer or curable component of the composition according to the present invention.

Preferably, PNPs according to the present invention are present in the form of a PNP concentrate in a carrier selected from the group consisting of at least one polymer, at least one curable component, and mixtures and combinations thereof. Because crosslinked PNPs according to the invention are typically non-film forming, they cannot be handled, pumped, drained, or flowed in the molten state. If the PNP is dissolved in a polymer or curable resin, the PNP concentrate is film forming and can be pumped in a molten state, chilled, and chipped or granulated. A PNP concentrate may be made by adding the polymer or curable resin of the present invention to a PNP solution, followed by dissolving the polymer or curable resin therein to produce a new solution which can now be dried down by conventional means, e.g. distillation, wiped film evaporation, drum drying, falling strand devolatilization or extrusion devolatilization. To minimize drying time and expense, the PNP solution can be concentrated by removal of some solvent before addition of polymer or curable component. Once the PNP is isolated from a solution of carrier and PNP, the PNP is well dispersed and much easier to blend into any coating, film-forming or molding formulation. Further, PNPs in PNP concentrates will re-disperse as individual particles when any resin matrix or polymer or curable component is made to flow, e.g. by melting or by adding solvent, by dispersing in a coating medium such as water, or by incorporating lubricant.

Alternatively, PNPs may be predispersed as a solid in the melt of a resin or thermoplastic polymer or in a liquid resin, followed by cooling the melt or by extending the liquid to form a resin that is solid at room temperature and cooling, and, optionally, grinding the cooled product to form a powder. PNP dispersions and ground PNP concentrates may comprise powders large enough to avoid handling and dusting problems, usually 20 to 400 microns in average particle diameter. The carriers as the matrix phase, and not the PNPs, determine whether the PNP concentrate or polymeric dispersion is storage stable as a solid or is adequately hard as a coating, film or article product. The carrier used to make a PNP concentrate or polymeric dispersion may comprise any polymer or curable resin that is compatible with the PNP and is soluble in one of the PNP solvents. Included may be epoxy resins, acrylic polymers, polyester resins, acrylic resins, polyurethane resins, ethylene polymers and copolymers including polyethylene waxes and oxidized polyethylene waxes, polyolefins, styrene polymers and copolymers, including styrene-acrylonitrile (SAN), styrene-methacrylate (SMA), and acrylonitrile-butadiene-styrene (ABS), and phenoxy resins. Preferably the carrier is a material that is used in a coating or molding formulation as a resin or curable component and has good flow, e.g. a viscosity of less than 5,000 centipoises, at low temperatures, i.e. below 150 C, preferably below 120 C. Examples of preferred carriers are epoxy resins, low molecular weight acrylic polymers and resins, and polyester resins, especially carboxyl, hydroxyl, or vinyl functional polyesters. While any amount of PNPs can be used for preparing PNP polymeric dispersions or PNP concentrates, it is preferred to employ levels of 10 to 90 percent, preferably 20 to 80 percent, and more preferably 40 to 60 percent PNPs, based on the total weight of the PNPs and the carrier. High PNP loading amounts may detrimentally affect film-forming or molding performance, while excessively low amounts of PNPs do not provide compositions which can form a film, coating or article having satisfactory damage resistance.

Coatings, films or articles of manufacture according to the present invention may comprise one or more polymer or curable components and from 0.5 to 30 weight % of crosslinked PNPs or crosslinked PNP particle dispersions or PNP concentrates. Preferably, said coatings, films or articles of manufacture comprise 2-15 weight % crosslinked PNPs or crosslinked PNP as particle dispersions or PNP concentrates, more preferably from 5 to 15 weight % of crosslinked PNPs or crosslinked PNPs as particle dispersions or PNP concentrates, most preferably from 10 to 15 weight % of crosslinked PNPs or crosslinked PNPs as particle dispersions or PNP concentrates. Said PNPs may comprise part of a powder coating or powder molding composition, liquid coating or floor care composition, liquid film forming or laminating composition or a liquid casting composition. In a method according to the present invention, PNPs are added to coatings, films, and articles of manufacture, preferably by incorporating PNPs or PNP polymeric dispersions or PNP concentrates into compositions from which the coatings and films are then formed. Alternatively, PNPs may be added to a film, coating or article of manufacture already formed by coating a layer of a PNP containing composition onto the film, coating or article of manufacture and curing or drying to form the coating.

The following non limiting examples are presented to illustrate the utility of the present invention.

EXAMPLE 5

Automotive Coatings

Automotive coatings comprising the outermost automotive coating (both metal and plastic parts) and interior automotive coatings are subject to damage caused by a variety of elements. These damages include exposure to environmental elements, such as high temperatures, high humidity, ultraviolet radiation, acidic precipitation, and contact with objects that cause scratching. Typically a harder coating exhibits improved scratch resistance but is less flexible and more susceptible to chipping and/or thermal cracking. A softer coating while not prone to chipping or thermal cracking, is more susceptible to scratching and acid etch. PNP's may be used alone or in combination with inorganic nanoparticles in clearcoat automotive coating compositions, pigmented automotive coatings, and UV curable automotive coatings to give a coating that is highly resistant to damage.

A representative damage resistant automotive coating composition can be obtained by using the PNPs of the present invention in place of inorganic particles in a clearcoat composition as described in EP0832947A2, Examples 3A-3C.

A representative damage resistant automotive coating composition can be obtained by using the PNPs of the present invention in addition to the inorganic particles in a clearcoat composition as described in EP0832947A2, Examples 3A-3C A representative PNP/pigmented automotive coating contains:
a) 10-100 parts by weight of a suitable polymer or polymer emulsion which may or may not be subsequently crosslinked.
b) 0.01-25 parts by weight of polymer solids, wetting, emulsifying, dispersing agents, defoamers, leveling agents, plasticizers, coalescing solvents, and additives sufficient for film formation and physical performance properties.
c) 0-90 parts by weight thickeners and/or other flow and shear control agents.
d) 0-90 parts by weight pigmented dispersion.
e) Water or any other suitable solvent to reduce solids to appropriate level as dictated by application technique.
f) 1-20 parts by weight of PNP material alone or combined with inorganic nanoparticles.

The total of a), b), c), d), e), and f) should be 100.

A representative UV curable/PNP automotive coating contains:
a) 10-100 parts by weight of a suitable acrylated oligomer, polyester oligomer, epoxide resin or other suitable polymer.
b) 0-90 parts by weight acrylated monomer.
c) 0-90 parts by weight of a suitable solvent and/or water to reduce solids to appropriate level as dictated by application technique.
d) 0-50 parts by weight of a suitable photoinitiator.
e) 0-90 parts by weight of a suitable flow control, wetting, dispersing agent, leveling agent, plasticizer, optical brightener, or other additive as deemed necessary.
f) 0-50 parts by weight of suitable light stabilizers including but not limited to UVA's and/or HALS as required to provide adequate UV protection as determined by product end use.
g) 1-20 parts by weight of PNP material alone or combined with inorganic nanoparticles.

The total of a), b), c), d), e), f, and g) should be 100

EXAMPLE 6

Nail Polish

PNPs may be used alone or in combination with inorganic nanoparticles in aqueous nail polish compositions. Currently, most nail polish compositions have as their base carrier an organic solvent. Due to health concerns from the flammability issues and the contacting of skin with organic solvents there has been research focused on the development of aqueous based nail polish compositions. Key to the development of an aqueous based nail polish is producing a coating that is damage resistance and resists scratching and marring. Such efforts are disclosed in U.S. Pat. No. 5,538,717 which is incorporated by reference. The use of PNP alone or in combination with inorganic nanoparticles in an aqueous nail polish composition allows for a coating that is highly resistant to damage.

A representative damage resistant coating composition can be obtained by using acrylic PNP in addition to the anionic polyester-polyurethane particles in an aqueous nail polish composition as described in U.S. Pat. No. 5,538,717, Examples 1-5. Another representative damage resistant coating composition can be obtained by using acrylic PNP in place of the anionic polyester-polyurethane particles in an aqueous nail polish composition as described in U.S. Pat. No. 5,538,717, Examples 1-5.

EXAMPLE 7

Floor Polish

PNPs may be used in floor polish compositions according to the present invention. PNPs provide floor finishes which are durable, have black heel and scuff mark resistance, good gloss, leveling, recoatability, alkaline detergent resistance, removability, water resistance, and storage stability.

Further, the use of PNP alone or in combination with inorganic nanoparticles in a floor polish composition allows for a coating that is highly resistant to damage. A representative floor polish composition according to the present invention may comprise the following main components:

a) 10-100 parts by solids weight water insoluble polymer which has been previously or subsequently crosslinked with a polyvalent metal complex and/or alkali metal basic salt;
b) 0-90 parts by solids weight wax emulsion;
c) 0-90 parts by solids weight alkali soluble resin (ASR), an acid-functional polymer;
d) 0.01-20 parts by weight of polymer solids wetting, emulsifying and dispersing agents, defoamer, leveling agent; optical brighteners, plasticizers and coalescing solvents, sufficient for polish film formation at application temperature;
e) water, sufficient to make total polish solids 0.5% to 45%, preferably 5% to 30%.
f) 1-20 parts by solids weight of PNP material, preferably the same PNPs as are used in powder coatings.

The total of a), b) and c) should be 100. The amount of c), when present may be up to 100% of a) and is preferably from 3% to 25% of the weight of a). An ASR is not an essential component of a durable floor polish composition. Depending on the properties inherent to the polish vehicle composition and other formulation ingredients (d), the ASR may optionally be employed to moderately reduce total formulation costs, improve leveling and gloss properties, and increase the polish sensitivity to alkaline strippers, depending upon the ultimate balance of properties desired by the polish formulator and qualities of ASR. For a high speed burnish polish compositions, the wax level should preferably be more than 6% by weight of the total solids of a), b) and c).

A polyvalent metal ion and complex crosslinking agent may be incorporated into the polish composition at any stage of its formulation. The polish composition need not contain a polyvalent metal ion if the end use calls for a metal free coating. The PNP material may be incorporated into the floor polish composition at any stage of its formulation. Similarly, the basic salt of the alkaline metal may be incorporated with the polyvalent metal ion and complex crosslinking agent at any stage of the floor polish formulation.

In addition to the PNPs the floor polish composition may contain other mar improving agents such as polyurethane dispersions.

EXAMPLE 8

Powder Coatings

A non limiting, representative powder coating of the present invention comprises 0.5-30 weight % of crosslinked PNPs having a mean diameter of 1 to 100 nanometers and a binder selected from the group consisting of epoxy resins, one-component epoxy resins, polyester resins, acrylic resins, polyester-acrylic hybrid resins, polyester-epoxy hybrid resins, silicon-containing resins, and combinations thereof. Polyester resin binders may include ultraviolet light (UV) curable unsaturated polyesters, preferably having maleate and fumarate unsaturation, or a mixture thereof, for on-mold coatings, in-mold coatings and low temperature cure applications.

In a preferred embodiment of the present invention, the PNPs used in the powder coatings do not react with the binder resin or polymer which makes up the powder coating. For example, PNPs preferably do not contain acid groups when used in any epoxy, hydroxyl group containing acrylic or polyester, or silicon resin containing powder coating and do not contain any hydroxyl groups in any polyester, urethane, or acid-functional acrylic containing powder coating.

Preferably, specific PNPs for use in damage resistant powder coatings are MMA or BMA PNPs having TMPTMA, EGDMA, ALMA, diethyleneglycol dimethacrylate (DEGDMA), and propyleneglycol dimethacrylate crosslinkers. A specific preferred PNP of the present invention is the PNP produced in EXAMPLE 2 of the present invention.

In a preferred embodiment of the present invention, PNPs or PNP particle dispersions are predispersed in melted or liquid resins or polymers for use in powder coatings, e.g. epoxy resins, which are then solidified by cooling or, alternatively, by chain extension, e.g. by reacting epoxy resin with a diphenol, and cooling, followed by grinding at room temperature. The resin matrices into which the PNPs are dispersed preferably have a softening point, melting point or Tg of 100 degrees C or lower to facilitate mixing. Because of the non-film forming nature of the PNPs, the PNPs will re-disperse as individual particles when any resin matrix or polymer or curable component is made to flow, e.g. by melting.

In a preferred powder coating of the present invention, the PNP containing powder coatings are cured at between 225 degrees F and 300 degrees F for use in coating heat-sensitive substrates and comprise a one-component powder made from a single melt blend or extrusion product of a curable component mixture of an epoxy resin having a melt viscosity of from 200 to 2000 centipoise at 150° C. and a curing agent which is solid at 80° F. and latent at an extrusion temperature of from 160° F. to 220° F. The term "one component coating powder" means that the powder is fully formed by grinding and screening only one extrudate of a mixture of the resin, curing agent, catalyst, and additives.

Epoxy resins are suitable curable components of powder coatings according to the present invention. Mixtures of epoxy resins may be used. A suitable mixture may comprise an epoxy resin having an equivalent weight between 100 and 400 and one having an equivalent weight between 400 and 1200 in a weight ratio of from 1:99 to 99:1. The resins are exemplified by, but not limited to, those produced by the reaction of epichlorohydrin and a bisphenol, e.g., bisphenol A and bisphenol F. The low melt viscosities of these resins facilitate the extrusion of them in admixture with a curing agent, additives and pigments at 160-220° F. The preferred melt viscosity is from 300 to 2000 centipoise at 150 degrees C. The melt viscosity of resins having a low T., i.e., from 35° C. to 55° C., is suitable for the purposes of this invention. Epoxy resins known as EPN (epoxy phenol novolac) and ECN (epoxy cresol novolac) resins and those made by the reaction of isopropylidenediphenol (bisphenol A) with epichlorohydrin are suitable for the purposes of this invention. These resins may comprise part of a PNP particle dispersion or may contain PNP particle dispersions.

The use of a crystalline epoxy in powder coatings according to the present invention may improve the flow characteristics of the fused coating powder and, therefore, the smoothness of the fused and cured coating. A particularly desirable flow is achieved when a crystalline epoxy constitutes from 5 to 20% by weight of the total amount epoxy resin used. However, the performance of a coating powder deteriorates as the level of crystalline epoxy resin therein is increased above 10% by weight because of the relatively low equivalent weights of such resins. A crystalline epoxy resin having a melting point between 80° C. and 150° C. is preferred.

Low temperature curing agents are preferred. They are active at a temperature of from 225 to 300° F. Epoxy adducts of an aliphatic polyamine (including cycloaliphatic polyamines) having a primary, secondary, or tertiary amino group or a combination of such amino groups are suitable curing agents for the purposes of this invention. An epoxy adduct of an aromatic polyamine, such as methylene dianiline, is also a suitable curing agent for the purposes of this invention. It is preferred that the functionality of the adducting reaction mixture is 2 or less and it is particularly preferred to use a difunctional epoxy compound. The amount of low temperature curing agent is from 2 to 40 parts per hundred parts of the resin (phr) and the preferred amount is from 5 to 20 phr. Increasing levels of the curing agent reduce the gel time and, therefore, increase the orange peel effect.

In powder coatings according to the present invention, a catalyst may be used at a level of from 0.1 to 5 parts per hundred parts of the resin, preferably 0.2-2 phr to accelerate the curing reaction with the low temperature curing agent. Preferred catalysts for this invention may be epoxy resin adducts of polyamines, such as LMB 5218 (Ciba Geigy), ANCAMINE® 2337 XS, 2014 AS or 2441 (Air Products and Chemicals), imidazoles and epoxy adducts thereof. Examples of suitable imidazoles include imidazole, 2-methyl imidazole, and 2-phenyl imidazole. For enhanced color stability a 2-phenyl imidazole is preferred.

Various gloss levels for the cured powder coating may be achieved through the choice of epoxy resins, curing agents, curing catalysts and the relative amounts of each. A low gloss may be achieved, for example, by the use of a slow acting curing agent (a dicyandiamide) and a fast acting agent (a substituted urea) to set up competitive reactions. Curing temperatures in the range of 110-140° C. (230-280° F.) may be achieved with such one-pack systems. The family includes phenyl dimethyl urea, toluene bis dimethyl urea, methylene bis (phenyl dimethyl) urea, and a cycloaliphatic bisurea.

The choice of curing agent for a low gloss powder coating is expanded by the use of acid-functional resins as matting agents in the formulation of the coating powders of this invention. For example, the P-101 imidazole/epoxy resin adduct named as a catalyst hereinabove may be used as a curing agent when such matting agents are used. An accelerated dicyandiamide may also be used as a curing agent at low temperatures in the presence of such matting agents to produce low gloss coatings. The amount of low temperature curing agent may also be reduced somewhat in the presence of the acidic matting agents and this, too, has the effect of reducing gloss. The smoothness attained by the incorporation of a crystalline epoxy resin, as noted hereinabove, may also be attained in the absence of such a resin when a matting agent is used.

Examples of such matting agents include, without limitation, an acrylic resin having an acid number of 142±5, a polyester having an acid number of 320, an acid-functional acrylic resin, and a low molecular weight, tetracarboxyl-functional polyester. The amount of matting agent is from 2 phr to 20 phr, preferably from 5 to 15 phr.

The coating powder may also contain a flow control agent in the range of from 0.5 to 2.0 phr. Examples of the flow control agents include, poly(alkylacrylate), acetylenic diols. They may be used singly or in combination. Anti-oxidants may also be used at a concentration of from 0.5 to 2.0 phr to prevent the discoloration of the coatings even at the relatively low curing temperatures suitable for the purposes of this invention. Examples of the anti-oxidants that are useful in this invention include sodium hypophosphite, tris-(2,4-di-t-butyl phenyl) phosphite, and calcium bis([monoethyl(3,5-di-t-butyl-4-hydroxybenzyl)phosphonate]. Mixtures of antioxidants may be used.

Pigments, optical brighteners, fillers such as calcium carbonate and bentonite clays, texturizing agents such as particulate rubber, and other conventional additives may also be present. A particularly desirable textured finish may be obtained by the addition of from 14 to 20 phr of the rubber to the coating composition along with calcium carbonate at a rubber to carbonate ratio of from 0.7:1 to 1.5:1 by weight. Titanium dioxide, in an amount of from 5 to 50 phr or more, is an example of a pigment that may be used. An optical brightener such as 2,2'-(2,5-thiophenediyl)bis[5-t-butylbenzoxazole] may be present at from 0.1 to 0.5 phr.

The particular utility of the powder coating composition of the present invention in the coating of heat sensitive substrates such as plastics, paper, cardboard and woods makes it highly appealing as a commercially viable alternative to the liquid coatings that have been almost universally used in the past. For the purposes of this invention, wood is defined as any lignocellulosic material whether it comes from trees or other plants and whether it be in its natural form, milled, or made into plywood, particle board, or fiberboard of various densities. It is exemplified by lumber, panels, molding, siding, oriented strand board, hardboard, and medium density fiberboard (MDF). The particle board may be standard or treated to enhance its electrical conductivity. Wood having a moisture content of from 3 to 10% by weight is suitable for the purposes of this invention. A porous particleboard, pre-coated with a conductive liquid coating composition and cured, may also serve as a substrate for the coating powder of this invention. For example, a smooth 2-3 mil thick powder coating is achieved on a 0.5 to 1 mil thick UV or thermally cured pre-coat.

The coating powder of this invention may be applied by any of the conventional powder coating methods, including electrostatic spray, fluidized bed application, and magnetic brush application, with the latter being used when the PNPs are used as a binder in very thin film applications. Electrostatic spray application is preferred.

EXAMPLE 9

Articles of Manufacture

PNPs may also be used to make articles of manufacture. Articles of manufacture are formed by extrusion molding or injection molding or film casting, or combinations thereof where a film is cast onto a molded article and cured or a female mold and the mold is filled with material and molding and film are cured. In a method according to the present invention, PNPs are added to articles of manufacture, preferably by incorporating PNPs or PNP polymeric dispersions or PNP concentrates into compositions from which the articles are then formed.

EXAMPLE 10

Binders

Crosslinked PNPs may also be used as binders for powder coatings, molding compositions, liquid coatings, floor care compositions, film forming or laminating compositions at levels of 30 to 90 weight % on a solids basis. PNP binder compositions may be used to provide very thin damage resistant films and coatings, such as in-mold or on-mold coatings. In addition, PNP binder compositions may be used to provide high resolution coatings, such as a photomask in semiconductor photolithography, by applying the compositions to a surface and curing to coat an area as narrow as from 1 micron to 1 mil (0.001 inch) in width.

We claim:
1. A method for imparting damage resistance to a coating, film or article of manufacture comprising adding crosslinked polymeric nanoparticles (PNPs) in combination with inorganic nanoparticles, said PNPs and said inorganic nanoparticles having a size range of 1-100 nm in diameter, to said coating, film or article of manufacture said PNPs having been formed by the free radical addition polymerization of a radical polymerizable monomer and at least one crosslinking monomer and having been crosslinked by using multi-ethylenically unsaturated crosslinking monomers, wherein said multi-ethylenically unsaturated crosslinking monomers were present prior to polymerization at a concentration or 5-85% by weight.

2. A damage resistant coating, film or article of manufacture comprising crosslinked polymeric nanoparticles (PNPs) in combination with inorganic nanoparticles, said PNPs and said inorganic nanoparticles having a size range of 1-100 nm in diameter, said PNPs having been formed by the free radical addition polymerization of a radical polymerizable monomer and at least one crosslinking monomer and having been crosslinked by using multi-ethylenically unsaturated crosslinking monomers wherein said multi-ethylenically unsaturated crosslinking monomers were present prior to polymerization at a concentration or 5-85% by weight.

3. A composition comprising: a carrier selected from one or more polymers and one or more curable components; and one or more crosslinked polymeric nanoparticles (PNPs) in combination with inorganic nanoparticles, wherein said PNPs and said inorganic nanoparticles have an average particle diameter of 1 to 100 nanometers, said PNPs having been formed by the free radical addition polymerization of a radical polymerizable monomer and at least one crosslinking monomer and having been crosslinked by using multi-ethylenically unsaturated crosslinking monomers wherein said multi-ethylenically unsaturated crosslinking monomers were present prior to polymerization at a concentration or 5-85% by weight.

4. A composition comprising inorganic nanoparticles and a crosslinked polymeric nanoparticle (PNP) concentrate comprising crosslinked polymeric nanoparticles (PNPs) dispersed in a carrier selected from the group consisting of at least one polymer, at least one curable component, and mixtures and combinations thereof, wherein said PNPs and said inorganic nanoparticles have an average particle diameter of 1to 100 nanometers, said PNPs having been formed by the free radical addition polymerization of a radical polymerizable monomer and at least one crosslinking monomer and having been crosslinked by using multi-ethylenically unsaturated crosslinking monomers wherein said multi-ethylenically unsaturated crosslinking monomers were present prior to polymerization at a concentration or 5-85% by weight.

5. A method of making the composition of claim 4 comprising adding to said PNP concentrate said polymer or curable component to a solution, dispersion, suspension or emulsion of said PNPs in a solvent, and removing said solvent by drying.

6. A composition selected from the group consisting of a powder coating composition, a liquid coating composition, a floor polish composition, an automotive coating, a nail polish composition, a thermoplastic molding composition, a thermoplastic film-forming composition, and a liquid film-forming composition comprising one or more crosslinked polymeric nanoparticles (PNPs) having an average particle diameter of 1-100 nm and inorganic nanoparticles having an average particle diameter of 1-100 nm, said crosslinked PNPs having been formed by the free radical addition polymerization of a radical polymerizable monomer and at least one crosslinking monomer and crosslinked by using multi-ethylenically unsaturated crosslinking monomers wherein said multi-ethylenically unsaturated crosslinking monomers were present prior to polymerization at a concentration or 5-85% by weight.

7. The composition as claimed in claim 6, wherein said composition is a powder coating composition having a curable component selected from the group consisting of epoxy resins, one-component epoxy resins, polyester resins, acrylic resins, polyester-acrylic hybrid resins, polyester-epoxy hybrid resins, silicon-containing resins, and combinations thereof.

8. The composition of claim 3 wherein said PNPs comprise an average particle diameter of 1to 50 nm and said inorganic particles comprise an average particle diameter of 2to 50 nm.

9. The composition of claim 6 wherein said PNPs comprise an average particle diameter of 1to 50 nm and said inorganic particles comprise an average particle diameter of 2to 50 nm.

10. The composition of claim 3 wherein said inorganic particles are selected from the group consisting of clays, silica, silica sols, titanium dioxide, metals, metal oxides, metal nitrides, metal carbides, metal sulfides, metal silicates, metal borides, metal carbonates, zeolites and carbon nanotubes, and combinations thereof.

11. The composition of claim 6 wherein said inorganic particles are selected from the group consisting of clays, silica, silica sols, titanium dioxide, metals, metal oxides, metal nitrides, metal carbides, metal sulfides, metal silicates, metal borides, metal carbonates, zeolites and carbon nanotubes, and combinations thereof.

12. The composition of claim 4 wherein said PNPs comprise an average particle diameter of 1to 50 nm and said inorganic particles comprise an average particle diameter of 2to 50 nm.

13. The composition of claim 4 wherein said PNPs and said inorganic particles comprise 1-20 parts by weight based on a weight of the composition.

14. The composition of claim 4 wherein said carrier comprises at least one of epoxy resins, acrylic polymers, polyester resins, acrylic resins, polyurethane resins, ethylene polymers and copolymers, polyolefins, styrene polymers and copolymers, and phenoxy resins.

15. The composition of claim 3 wherein said carrier comprises at least one of epoxy resins, acrylic polymers, polyester resins, acrylic resins, polyurethane resins, ethylene polymers and copolymers, polyolefins, styrene polymers and copolymers, and phenoxy resins.

16. The coating, film or article of manufacture of claim 2 wherein said PNPs comprise 0.5 to 30 weight % of the coating, film or article of manufacture.

17. The coating, film or article of manufacture of claim 2 further comprising a carrier selected from the group consisting of at least one polymer, at least one curable component, and mixtures and combinations thereof.

18. The coating, film or article of manufacture of claim 2 wherein said carrier comprises at least one of epoxy resins, acrylic polymers, polyester resins, acrylic resins, polyurethane resins, ethylene polymers and copolymers, polyolefins, styrene polymers and copolymers, and phenoxy resins.

* * * * *